United States Patent [19]

Crosby

[11] 4,319,562
[45] Mar. 16, 1982

[54] METHOD AND APPARATUS FOR PERMANENT EPICARDIAL PACING OR DRAINAGE OF PERICARDIAL FLUID AND PERICARDIAL BIOPSY

[75] Inventor: Ivan K. Crosby, Charlottesville, Va.

[73] Assignee: The University of Virginia Alumni Patents Foundation, Charlottesville, Va.

[21] Appl. No.: 61,408

[22] Filed: Jul. 27, 1979

Related U.S. Application Data

[62] Division of Ser. No. 865,173, Dec. 28, 1977, Pat. No. 4,181,123.

[51] Int. Cl.³ ............................................. A61B 19/00
[52] U.S. Cl. ..................................... 128/1 R; 128/751
[58] Field of Search .................... 128/1 R, 6, 668, 751

[56] References Cited

PUBLICATIONS

Davis–Christopher, *Textbook of Surgery*, 1972, pp. 1888–1889.

*Primary Examiner*—Stephen C. Pellegrino
*Attorney, Agent, or Firm*—Oblon, Fisher, Spivak, McClelland & Maier

[57] ABSTRACT

A method and apparatus for providing permanent epicardial pacing comparable to permanent transvenous pacing in the acutely ill or debilitated patient under local anesthesia and for drainage of pericardial fluid and pericardial biopsy. The apparatus includes a cylindrical member with first and second open end portions, an inner and outer wall portion and a connecting slot between the inner and outer wall portions, a guard member provided at the first end portion of the cylindrical member adjacent to the slot and a maneuvering member connected to the outer wall portion at the second end portion of the cylindrical member. The epicardial pacing method includes the steps of making a keyhole incision below a xyphoid process of a body, introducing a pericardioscope into a retro-sternal space of the body, making a cruciate incision in the pericardial cavity of the heart, screwing myocardial electrodes into a right ventricle of the heart, removing the pericardioscope from the retro-sternal space; attaching electrodes subcutaneously into a pocket in the left upper quadrant of the abdomen, and attaching a pulse generator to the electrodes to thereby provide epicardial pacing. The method of drainage of pericardial fluid and pericardial biopsy includes the steps of making a keyhole incision below a xyphoid process of a body, introducing a pericardioscope into a retro-sternal space of the body and excising a disc of the pericardium so as to allow for drainage of the pericardial fluid, entrance of the pericardioscope into the pericardial cavity, inspection of the epicardial surface of the heart and evaluation of the pericardium itself.

1 Claim, 2 Drawing Figures

METHOD AND APPARATUS FOR PERMANENT EPICARDIAL PACING OR DRAINAGE OF PERICARDIAL FLUID AND PERICARDIAL BIOPSY

This is a division, of application Ser. No. 865,173, filed Dec. 28, 1977, now U.S. Pat. No. 4,181,123.

BACKGROUND OF THE INVENTION

1. Field of the Invention

This invention relates to a method and apparatus for providing permanent epicardial pacing comparable to permanent transvenous pacing in the acutely ill or debilitated patient under local anesthesia as well as for providing drainage of pericardial fluid and pericardial biopsy.

2. Description of the Prior Art

The medical treatment of symptomatic atrioventicular conduction defects is known to be fraught with difficulties and uncertainties. As a result, long-term electrical stimulation has gained wide acceptance. Three basic methods of myocardial stimulation have been used successfully: external stimulation through the chest wall, transvenous electrode catheter stimulation, and permanent myocardial electrode stimulation. Each method of electrical stimulation of the myocardium has been shown to suffer from some imperfection, either inherent in the method of stimulation or caused by the reaction of local tissue to the electrode.

Conventional techniques for pericardial biopsy and drainage of pericardial fluid include a left thoracotomy, and direct attack on the left side of the pericardium, through the thoracotomy incision, for conventional biopsy and drainage of the fluid; the left chest cavity then being drained via a chest tube. The second conventional approach is excision of the xiphoid process through a larger, midline incision and direct biopsy of the pericardium after grasping the pericardium with a surgical clamp. The pericardial cavity is then drained if necessary, with a tube introduced through this xiphoid incision.

The advantages of the present invention over currently available epicardial techniques are the avoidance of a thoracotomy incision, a chest tube and general anesthesia, or, if local anesthesia is used, avoidance of xyphoid process removal and its attendant postoperative pain. The advantages over transvenous pacing include reduction of early and late wound problems and marked reduction in early and late failure-to-capture problems.

The main advantage of pericardioscope biopsy and drainage is that a tiny surgical incision is made and minimal discomfort is experienced by the patient.

SUMMARY OF THE INVENTION

An object of this invention is to provide a method and apparatus which allows for permanent epicardial pacing comparable to permanent transvenous pacing and to provide for minimal discomfort to the patient during drainage of pericardial fluid and pericardial biopsy.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENT

Figure 1:
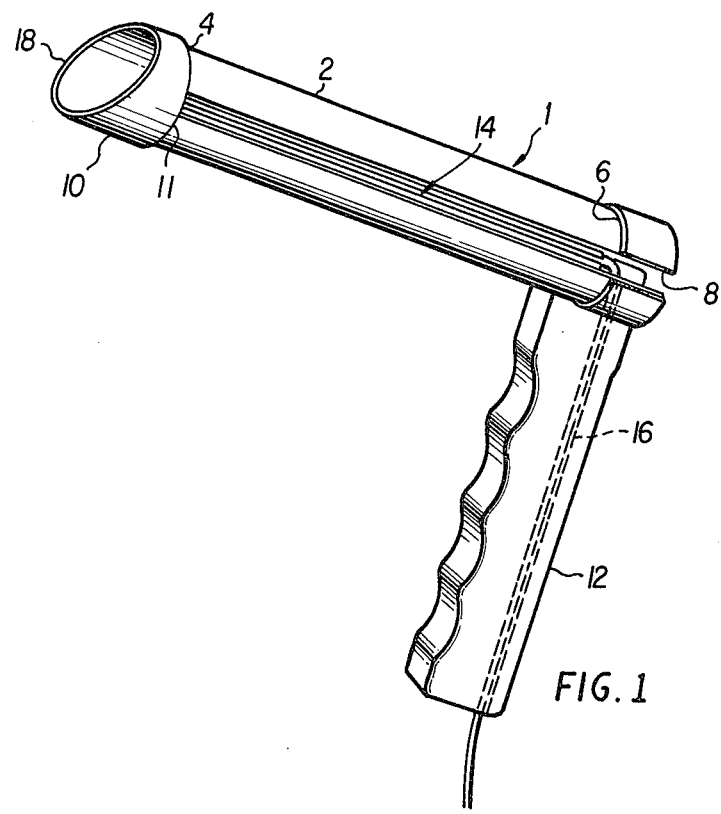
FIG. 1 is a perspective view of the present invention.

The invention will be described in greater detail hereinafter with reference to FIG. 1. The pericardioscope 1 includes a cylindrical member 2 which includes a first and second open end portion, 4 and 6 respectively, an inner and outer wall portion, and a slot 8 connecting the inner and outer wall portions. Slot 8 both extends between the first and second open end portions of cylindrical member 2 and connects the inner and outer wall portion thereof.

Figure 2:
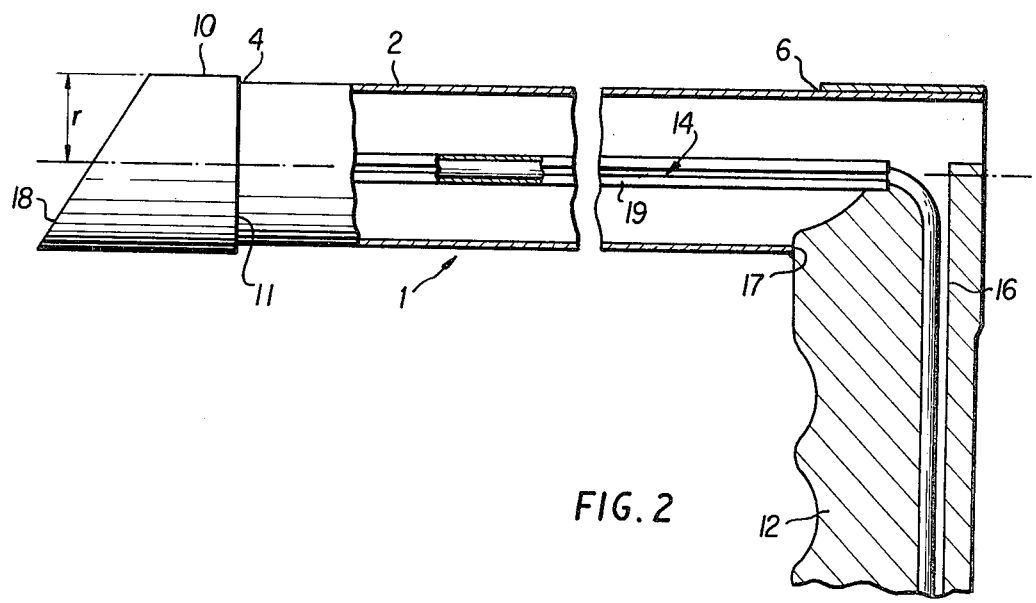
FIG. 2 is a perspective view of the upper portion of the embodiment of FIG. 1.

A guard or shield element 10 is secured to the first end portion 4 of cylindrical member 2. Guard element 10 further includes an outer surface radius r which is greater than the radius of cylindrical member 2. It can thus be seen that slot 8 terminates at edge portion 11 of guard element 10 at first end portion 4. A bevelled tip portion 18 is also provided at one end of guard element 10 which forms a slope angle of approximately 60° with respect to the longitudinal axis of the cylindrical member indicated by the broken line in FIG. 2.

A maneuvering handle 12 also connects to second end portion 6 of cylindrical member 2. Pericardioscope 1 is approximately 16 cm. in length with an internal diameter of approximately 2.5 cm. and further includes a fiberoptic light source 14 which is connected to and extends along the inner wall portion of cylindrical member 2 at a position directly opposite to slot 8. The fiberoptic light source 14 includes at least one tubular member which extends from first open end portion 4 to second open end portion 6 of cylindrical member 2 and is provided adjacent guard member 10 with a bevelled tip which provides illumination at a point adjacent first open end portion 4. Handle member 12 also includes a slot 16 along its entire length which connects with an opening 17 in cylindrical member 2 to provide a housing and lead in channel for fiberoptic light source 14 which in turn is connected to a light generating element, not shown. Guide element 19 is used to channel fiberoptic light source 14 as shown. Pericardioscope 1 is advantageously constructed of metal which thus allows for easy sterilization.

The epicardial pacing process within which the pericardioscope is utilized is for the insertion of a pacemaker and the corresponding drainage of pericardial effusions. The process of providing permanent epicardial pacing utilizing a pericardioscope is characterized by making a small key-hole incision 3.6 cm. in length, under local anesthesia, below the xyphoid process. The pericardioscope 1 is then introduced into the retro-sternal space and, through a cruciate incision in the pericardium, into the pericardial cavity. Subsequently, sutureless myocardial electrodes are screwed into the right ventricle and the pericardioscope is then removed. The electrodes are brought subcutaneously into a pocket in the left upper quadrant where a pulse generator is attached and buried.

The advantages over currently available epicardial techniques are the avoidance of a thoracotomy incision, a chest tube and general anesthesia, or if local anesthesia is used, avoidance of a xyphoid process removal and its attendant postoperative pain. The advantages over transvenous pacing include reduction of early and late wound problems and marked reduction in early and late failure-to-capture problems.

The pericardioscope is also quite suitable for drainage of pericardial fluid and pericardial biopsy. To accomplish this, the same small key-hole incision is made below the xiphoid process and the scope is introduced into the retrosternal space. A disc of the pericardium (full thickness) is excised using the scope and its instrument kit. This, then allows drainage of the pericardial fluid, entrance of the scope into the pericardial cavity, and inspection of the epicardial surface of the heart, and evaluation of the pericardium itself.

Obviously, many modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A surgical method of drainage of pericardial fluid and pericardial biopsy, comprising:
   making a key hole incision below the xiphoid process of a body;
   introducing a pericardioscope through said key hole incision into a retrosternal space of said body; and
   performing pericardial biopsy by excising a disc of the pericardium, so as to allow for drainage of the pericardial fluid, entrance of the pericardioscope into the pericardial cavity, inspection of the epicardial surface of the heart and evaluation of the pericardium itself.

* * * * *